United States Patent [19]

Wyburn-Mason

[11] 4,119,723

[45] Oct. 10, 1978

[54] TREATMENT OF RHEUMATOID ARTHRITIS AND RELATED DISEASES

[75] Inventor: Roger Wyburn-Mason, Richmond Surrey, England

[73] Assignee: John R. A. Simoons, Summit, N.J.

[21] Appl. No.: 813,922

[22] Filed: Jul. 8, 1977

[51] Int. Cl.² ........................................... A61K 31/415
[52] U.S. Cl. ............................................... 424/273 R
[58] Field of Search ........................................ 424/273

[56] References Cited

U.S. PATENT DOCUMENTS 3,376,311  4/1968  Butler .................................. 548/338

*Primary Examiner*—Stanley J. Friedman
*Attorney, Agent, or Firm*—Richard T. Laughlin

[57] ABSTRACT

It is believed that rheumatoid arthritis and related collagen and auto-immune diseases are an infection and that various species of free-living (limax) amoebae are the aetiological agent of these diseases. It has been discovered that tinidazole and related compounds, antimycotic drugs with anti-protozoal activity, are effective for the treatment of rheumatoid arthritis and other collagen and auto-immune (rheumatoid) diseases.

5 Claims, No Drawings

TREATMENT OF RHEUMATOID ARTHRITIS AND RELATED DISEASES

BACKGROUND OF THE INVENTION

Men and other animals are continually exposed to infection and re-infection by various species and strains of free-living limax amoebae which can be detected in the faeces, nasopharynx and bronchi. In all parts of the world they form part of the environment. Experimentally in animals they induce changes like those of collagen and auto-immune diseases and are characterized by vasculitis, myosotis, hepatitis, pyelitis and spelenomegaly. They can often be seen in the tissues of animals. Such animals shown lymphadenopathy with an appearance like that of human Hodgkin's disease or a state like that of advanced malignant disease. These organisms may also be recovered from all the tissues of cases of collagen and auto-immune diseases and from human and many animal tumors and may also occur in the tissues of apparently healthy individuals. They cannot be identified in ordinary histological sections, but can be demonstrated by immunofluorescent methods.

The definite cause of rheumatoid arthritis is presently unknown. Rheumatoid arthritis is a crippling disease, characterized by the inflammation of several joints of the body, with swelling, pain and stiffness. Rheumatoid arthritis is a disorder that afflicts about fifteen million people in the Western World alone. Successful early treatment may avert the destructive, deforming phase of the disease. Therapy has been directed largely at non-specific suppression of inflammatory and immunoligic processes. Aspirin is the cornerstone of therapy for rheumatoid arthritis and can reduce synovial inflammation, improve function and reduce pain in a majority of patients in view of its analgesic action. Widespread interest in rheumatoid arthritis arose when Hench (1949) introduced the use of cortisone in treatment. Chemical compounds which have been commonly used in treating rheumatoid arthritis are corticosteroids, gold salts, antimalarial drugs, immunosuppressive agents and a whole range of so-called non-steroidal drugs, e.g. indomethacin, phenylacetic acid (Ibuprofen), propionic acid (Naproxen) and D-Penicillamine. Most of these drugs bring temporary relief to the arthritic patient but present the danger of side effects and the physician has to balance the potential benefit against the risks. However, arthritis reoccurs following withdrawal of such chemical treatment. For many years rheumatoid arthritis was considered to be an infection (Hollander et al., 1960; Robinson, 1967), but with the advent of the concept of auto-immunity this idea lost favor. Such a view has recently been revived (Lancet, 1970, 2, 303) and is supported by many observations. It is highly likely that the limax amoebae, found in all the collagen and auto-immune diseases, may well be the aetiological agent of these conditions and that antiprotozoal drugs may help by their action on these organisms.

The use of a bis-phenyl (2-halophenyl)-1-imidazolylmethane and clotrimazole for treatment of Rheumatoid Arthritis is disclosed in my U.S. patent application Ser. No. 700,914 filed June 29, 1976. It has also been suggested to use a nitroimidazole in the treatment of rheumatoid arthritis in the Journal of Tropical Medicine and Hygiene (vol. 75) pgs. 64 to 66 March 1972. It is believed that the nitro group in the imidazole ring is related to metronidiazole which is not effective in the treatment of rheumatoid arthritis.

Tinidazole and related compounds for use as antiprotozal agents is disclosed in a number of articles such as pages 257 to 259 of Antimicrobial Agents and Chemotheraphy-1969 (copyright 1970 American Society for Microbiology (Miller, Howes & English) & Current Medical Research and Opinion, vol. 2, No. 3, pages 178 to 179 (article entitled "Single-dose treatment of vaginal trichomoniasis with tinidazole ('Fasigyn')" by Thavabalan and Oriel)

It has been found that certain imidazole compounds which have antiprotozoal activity are effective when administered internally for treating rheumatoid arthritis and related collagen and auto-immune (rheumatoid) diseases. Of this group compounds, tinidazole has proven most effective. This compound has the following chemical structural formula:

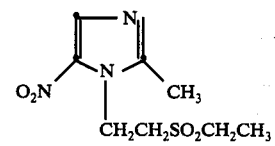

Various other anti-protozoal drugs were tried on the cases of rheumatoid disease or of various localized manifestations of this. The substances investigated were 4-aminoquinolines (chloroquine), hydroxychloroquine (plaquenil), amodiaquine (camoquin); copper sulphate; bile salts (dehydrocholine), which are effective in killing the trophozooites of many amoebae in the concentration found in the small intestine; and clotrimazole (canesten). All of these were actually shown experimentally to kill limax amoebae. In addition, other antiprotozoal drugs were also investigated. They included suramin, pentamidine, dehydro-emetine (DHE or mebadin), metronidiazole (flagyl), nitroimidazole (naxogin (Ergba)), phanquone (entobex) and diloxanide (furamide).

The 4-aminoquinolines were given by mouth in a dose of 200 and 400 mg. daily, reduced after a month to 200 mg. twice weekly, care being taken to examine the eyes at intervals to guard against keratitis or macular changes. Copper salts were administered as 25 mg. of copper sulfate in aqua chloroformi by mouth three times daily. This may produce vomiting and/or diarrhea and the dose has to be decreased to 10 mg. three times daily. Only a small amount of the metal is absorbed, however, and no other side effects are observed even when taken over several months. Bile salts as dehydrocholine were given in a dose of 500–1000 mg. three times a day by mouth. They may produce mild colic. This may be prevented by simultaneous administration of a kaolin mixture. Pentamidine was at first given by intramuscular injection into the buttock in doses of 200 mg. daily for 10 days. The course was repeated twice with intervals of 7 days between. This substance is liable to produce local necrosis or abscess formation. Pentamidine can be given by mouth, but tis absorption is uncertain. Moreover, it may produce nausea, vomiting and diarrhea. However, many patients tolerate it by this route. Capsules containing 200 mg. were especially made and a dose of 200 mg. twice daily to 400 mg. three times daily by mouth were tried in various combinations. Suramin was given by intravenous injection of 500 mg. in 10 ml. of water and after this every 4 days 1 G was injected until 10 G had been given. The course was repeated once after 4 months. Dehydro-emetine(DHE) was given by intramuscular injection in doses of 60 mg. daily for 10 days and repeated after 7 days, or 60 mg. three times daily by mouth for 7-12 days, repeated after an interval of 10 days. Before commencing treatment E.C.G.'s were taken and repeated before each successive injection. Metronidiazole (flagyl) was given in doses of 400-600 mg. three times daily by mouth and nitromidazole (naxogin) in doses of 75 mg. three times daily. Phanquone (entobex) was given in doses of 100 mg. twice daily by mouth for 7 days, repeated at intervals of a week, Diloxanide (furamide) was given in doses of 500 mg. three times daily for 10 days and repeated once.

The various substances tested above were tried on cases of rheumatoid arthritis of varying severity, systemic lupus erythematosus, dermatomyositis and other manifestations of collagen and auto-immune disease and observations made on the clinical condition, oedema, morning stiffness, E.S.R., plasma proteins, RF, ANF and organ-specific antibodies in the serum. No attempt at a double-blind trial was made as it became obvious, fairly early or even the day after commencing treatment, whether beneficial effect was obtained and furthermore, symptomatic improvement is associated with improvement or disappearance of the abnormal blood changes, indicating that the drug was effective and improvement not due to suggestion. No beneficial effect was obtained from flagyl, naxogin, entobex, suramin or furamide in the doses used. However, Abd-Rabbo et al. (1972), using a derivative of nitro-imidazole (naxogin), BT 985 Merck A.G., which is active against amoebae, giardia and trichomonas, obtained beneficial effects in one case of systemic lupus erythematosus and nine of ten cases of rheumatoid disease. The drug was given in doses of 250 mg. daily for 14-39 days. In the follow-up period of 3-6 months no treatment was given and it was noted that the pain recurred, yet not to the same degree as before medication.

Tinidazole is an antimycotic drug, synthesized by Pfizer Medical Research Laboratories, Groton, Conn. (pgs. 257-260, Antimicrobial Agents and Chemotheray-1969) and known as "Fasigyn". It is chemically ethyl [2-(2-methyl 5-nitro-1-imidazolyl) ethyl] sulfone. It has been successfully used in the treatment of a number of protozoal diseases, such as amoebiasis, giardiasis and trichomonas infections.

The method of determining the anti-protozoal activity of drugs on limax amoebae was described by Fulton, C. Methods in Cell Biology (edited by D. M. Prescott), p. 341, New York, 1970 and followed by Jamieson and Anderson in Lancet, 1974, 1, 261. All experiments were preformed using 5-day-old 5 ml. cultures of amoebae in the axenic medium "A" of Fulton. A standard inoculum of 100 c.mm. of differing concentrations of amoebae was added to each 1 ml. tube containing the dilutions of the compound to be tested (disolved initially in dimethyl sulfoxide) or other drugs in the axenic medium. The tubes were incubated for 5 days and 37 C. and the final concentration per c.mm. was compared with the initial count to determine percentage kill.

It has now been found that rheumatoid arthritis can be effectively treated with compounds having antiprotozoal activity of the formula:

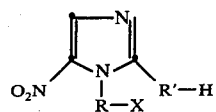

wherein R & R' are each alkylene having 1 to 7 carbon atoms and X is a lower alkylsulfonyl and the pharmaceutically acceptable acid addition salts thereof. Particularly effective compounds are those wherein R' is methylene. These compounds and their preparation, are disclosed in U.S. Pat. No. 3,376,311 issue Apr. 2, 1966 to Kenneth Butler. Typical of these compounds are:
 1-(2-ethylsulfonylethyl)-5-nitroimidazole
 1-(2-ethylsulfonylethyl)-2-methyl-5-nitroimidazole
 1-(2-propylsulfonylethyl)-2-methylnitroimidazole
 1-(2-methylsulfonylethyl)-2-methyl-5-nitroimidazole
 1-(2-isopropylsulfonylethyl)-2-methyl-5-nitroimidazole The salts of such N-trityl-imidazoles are the pharmaceutically acceptable non-toxic acid addition salts. Examples of suitable acids are the hydrohalic acids (hydrochloric being particularly preferred), phosphoric acid, mono-and bi-functional carboxylic acids, such as acetic acid, propionic acid, maleic acid, succinic acid, fumaric acid, tartaric acid, citric acid, salicylic acid, sorbic acid, lactic acid and 1.5-napththalene- disulphonic acid. The hydrohalides, especially the hydrochlorides, lactates and salicylates are of particular value.

The diagnosis of active rheumatoid arthritis in 25 cases, was consistent with the criteria of the American Rheumatism Association. The patients were not hospitalized or confined to bed. They continued to take the drugs they were being treated with when first seen. Serial investigations were carried out before and repeatedly during and after treatment. Tinidazole was administered orally in a dosage of four tablets of 500 mg. each once per week for ten weeks (approximately 35 mg. per kilogram of body weight) suitable doses range from about 20 to 50 mg. per kilogram of body weight. With this dosage of the drug beginning 24-36 hours after taking it there almost invariably occurs an exacerbation of the active inflammatory changes in the affected joints with increased heat, pain and swelling and other parts of the body not previously affected may also be involved with generalized malaise and often sweating. This may last for 2-3 days and then disappear with general improvement in the patients symptoms. With successive doses this reaction become less and finally disappears and as the course of treatment progresses the signs of active rheumatoid disease also disappear. Steroid and other treatments may then be tapered off. This response constitutes an Herxheimer reaction and its occurrence with Tinidazole, an antimycotic and antiprotozoal drug, indicates with certainty the presence in the affected tissues of an organism which is acted on by Tinidazole. This reaction does not occur when the drug is used in the treatment of amoebic dysentery or trichomonas infection. In order to obviate this reaction in later cases the dosage of Tinidazole was altered and reduced to 2 (500 mg.) tablets (1G) on alternate days. This dosage avoided the above reaction and was continued for 10 weeks with similar results to those obtained using the original manner of administration. By neither method is there reversal of bone or cartilage changes already present when treatment was begun. Tinidazole was administered to 10 males and 15 females, their ages ranging from 24–64 years. Symptoms had been present for 23 months to 33 years. Patients have been followed for 6–9 months without evidence of recurrence of activity of the disease and with return of the sedimentation rate to normal. The drug thus eventually completely reversed all the manifestations of activity in rheumatoid disease when other drugs had failed. In larger doses it may cause an Herxheimer response indicating the existence in the lesions of rheumatoid disease of an organism, presumably a protozoan, affected by the drug. It caused no other side effects except occasional pruritus when alcohol was taken.

The therapeutically effective compound can be used either as such or in combination with pharmaceutically acceptable carriers. Suitable forms of administration in combination with various inert carriers are tablets, capsules, powders, aqueous suspensions, syrups and the like. In the aforesaid case, the therapeutically active compound should be present in the total mixture at a concentration of about 0.5 to 90 percent by weight, i.e., in quantities which suffice to attain the range of dosage mentioned above. Tablets may also contain fillers such as starch, avicel, lactose, calcium carbonate or dicalcium phosphate together with various additives such as dyes and binders such as polyvinylpyrrolidine, methylcellulose, gelatin and the like. It is further required to add lubricants such as magnesium stearate, sodium lauryl-sulphate and talc for producing tablets. Tablets may be filmcoated.

EXAMPLE I

|  | Weight |  |
|---|---|---|
| Micronized tinidazole powder | 5.0 | Kg. |
| Cornstarch powder | 0.52 | Kg. |
| Avicel (microcrystalline cellulose)PH 102 | 1.8 | Kg. |
| Methocel 50 HG, 60 CPS | 100.0 | gm. |
| Purified water |  | q.s. |

The tinidazole powder is mixed in a suitable blender with the other components and then granulated mass is passed through an oscillator equipped with a 20-mesh screen. The granules are dried in an air circulating oven at 50° C. until a moisture content of less than 3% is reached. The granules are screened through a 20-mesh screen, lubricated with stearic acid 30 gm. and magnesium stearate 50 gm. The final mix is compressed into tablets of 750 mg. each, which contain 500 mg. of tinidazole per tablet and can be used for oral administration.

Any departure from the foregoing description conforms to the present invention is intended to be included within the scope of the claims.

What is claimed is:

1. A method for producing remission in patients suffering from active rheumatoid arthritis which comprises administering orally to such a patient an effective amount of a compound of the formula:

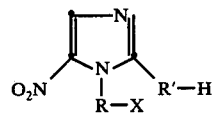

wherein R and R' are each alkylene having 1 to 7 carbon atoms and X is lower alkylsulfonyl and the pharmaceutically acceptable acid addition salt thereof.

2. The method of claim 1 wherein R is alkylene having 1 to 7 carbon atoms, X is lower alkylsulfonyl and R' is methylene.

3. The method according to claim 1 wherein the compound is tinidazole having the formula:

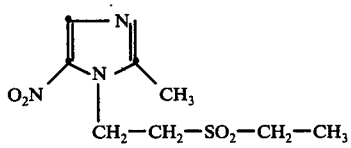

4. The method of claim 1, wherein the compound is tinidazole having the formula:

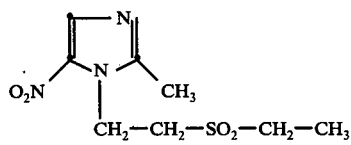

and is administered orally in doses of approximately 35 mg. per kilogram of body weight per week.

5. The method of combating rheumatoid arthritis of claim 4 which comprises orally administering to the infected subject tinidazole in a weekly dose amount of about 20 to about 50 miligrams per kilogram of body weight.

* * * * *